United States Patent

Masuda et al.

[11] Patent Number: 6,051,977
[45] Date of Patent: Apr. 18, 2000

[54] METHOD AND APPARATUS FOR LOCATING COATING FAULTS ON BURIED PIPELINES

[75] Inventors: Toshikazu Masuda, Tokyo; Toshio Osada, Tokyo; Shinji Gotoh, Kanagawa, all of Japan

[73] Assignee: Kawasaki Steel Corporation, Kobe, Japan

[21] Appl. No.: 09/007,775

[22] Filed: Jan. 16, 1998

[30] Foreign Application Priority Data

Jan. 22, 1997 [JP] Japan .................................. 9-009615

[51] Int. Cl.[7] .......................... G01N 27/82; G01N 27/83; G01R 33/02
[52] U.S. Cl. .......................... 324/529; 324/326; 324/559; 324/71.1
[58] Field of Search ................................ 324/66, 67, 239, 324/326, 329, 527, 528, 529, 531, 551, 557, 700, 71.1, 71.2, 240

[56] References Cited

U.S. PATENT DOCUMENTS

| | | | |
|---|---|---|---|
| 3,745,452 | 7/1973 | Osburn et al. | 324/529 |
| 4,134,061 | 1/1979 | Gudgel | 324/529 |
| 4,390,836 | 6/1983 | Bruce et al. | 324/529 |
| 4,839,593 | 6/1989 | Spies | 324/240 |
| 4,982,163 | 1/1991 | Viikari et al. | 324/240 |
| 5,087,873 | 2/1992 | Murphy et al. | 324/529 |
| 5,719,500 | 2/1998 | Eschner et al. | 324/329 |
| 5,828,219 | 10/1998 | Hanlon et al. | 324/529 |

FOREIGN PATENT DOCUMENTS

3-152411  6/1991  Japan .

OTHER PUBLICATIONS

"Pipe Coating Fault Locating Systemt for Buried Pipelines", A. Nagamune et al., The 30th Automatic Control Annual Meeting, vol. 4044, pp. 745–746 (Oct. 1987).

Primary Examiner—Diep N. Do
Attorney, Agent, or Firm—Oliff & Berridge, PLC

[57] ABSTRACT

A coating fault locating technique transmits a base electric signal from a power source to a buried metal pipe. A location of a coating fault in the buried pipe is detected by detecting a gradient of a changing magnetic field between two points spaced along the buried pipe. The gradient is detected based upon the output differential of at least one pair of search coils. The gradient is caused by a leakage of current that occurs at the coating fault. In particular, the at least one pair of search coils are provided in a mobile unit that is located above ground. The at least one pair of search coils are spaced apart from one another and have their axes arranged so as to have a low sensitivity to a magnetic field generated by the base electric signal running through the buried pipe. The at least one pair of coils are spaced apart from each other such that a line drawn between midpoints of the search coils' axes crosses a plane normal to the axis of the buried pipe. For example, the at least one pair of search coils are spaced from each other horizontally, with each coil arranged with its axis extending in a vertical plane. The data detected by the search coils in the mobile unit can be transmitted to a GPS system, which then generates a map identifying the locations of any detected coating faults.

24 Claims, 10 Drawing Sheets

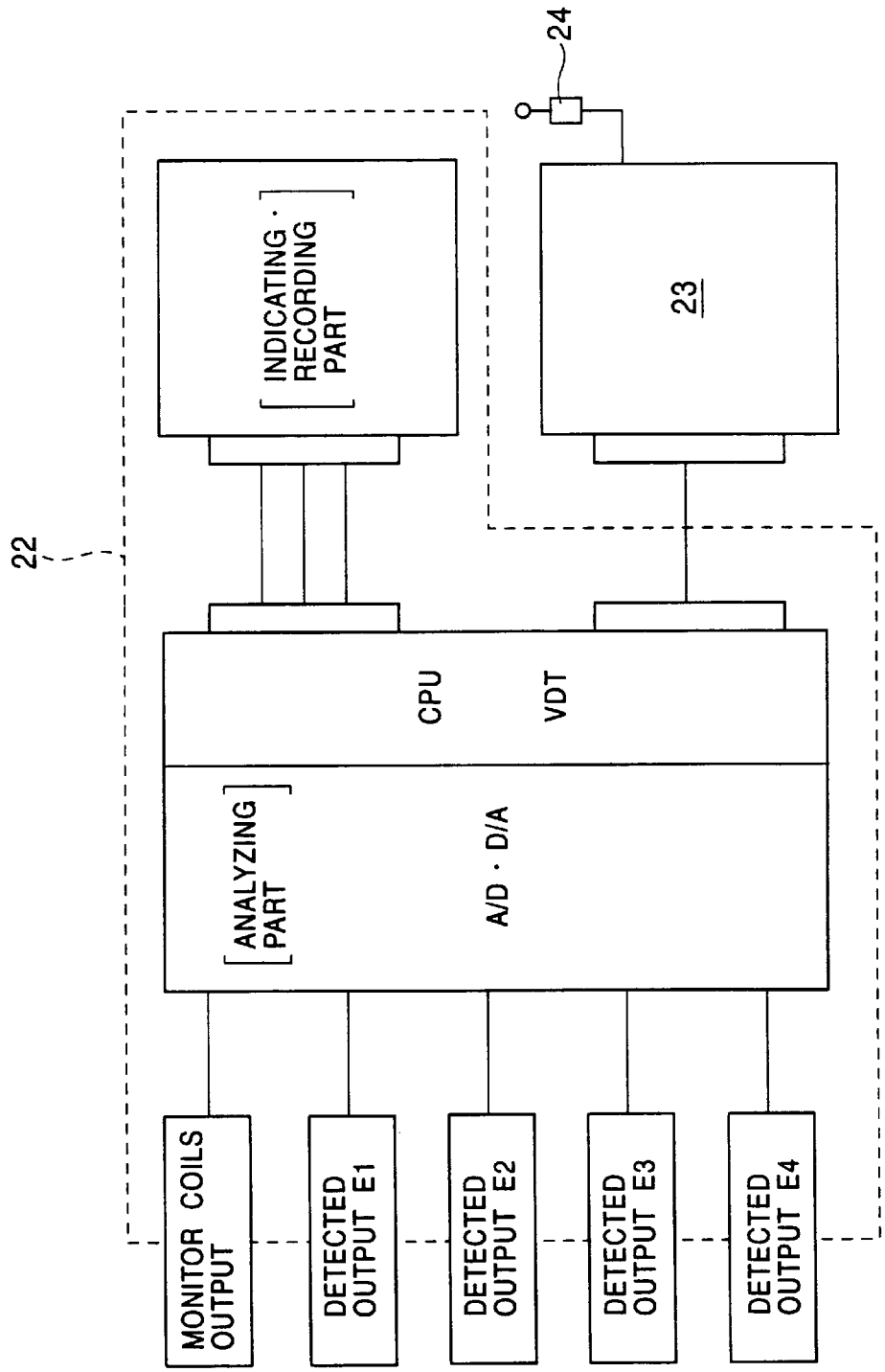

METHOD AND APPARATUS FOR LOCATING COATING FAULTS ON BURIED PIPELINES

BACKGROUND OF THE INVENTION

1. Field of Invention

The present invention relates to methods and apparatus for locating coating faults on buried pipelines, and in particular to such methods and apparatus that rely upon magnetic field detection.

2. Description of Related Art

Many steps are taken to prevent buried metal pipe (e.g., steel pipe) from being subjected to corrosion by, for example, electro-chemical reactions. For example, it is known to coat the surface of the steel pipe with a material and/or to keep the pipe's electric potential equal or lower to that of the ground.

In many instances, it is necessary to regularly check the condition of the pipe after it is buried to determine whether any corrosion of the pipe has taken place. This is particularly important when the buried pipe is, for example, a gas pipeline.

Accordingly, it is known to check the condition of buried gas pipelines from above the ground using electromagnetic searching techniques. Using such techniques, the location of coating faults in the pipeline or the location where the pipeline touches another buried pipe, for example a water pipe, can be detected.

The publication entitled The 30th Automatic Control Annual Meeting (4044, pages 745–746, October 1987) describes a searching system that combines soil-to-soil potential methods with magnetic field measuring methods to locate coating faults. In particular, a magnetic field change that is generated due to a coating fault in a buried pipeline to which a base electric signal is applied is detected in order to locate the coating faults. This technique is prone to difficulties and mistakes because the soil-to-soil potential method requires that an electric signal is run from the road surface.

Japanese Laid-Open Patent Application No. 3-152411 discloses a technique that locates coating faults using only magnetic methods. However, with this arrangement, it is difficult to locate the origin of leakage current (from coating faults) because the magnetic field generated by the leakage current is weak and the disclosed method is strongly influenced from environmental noise.

Additionally, these techniques involve processing and recording the data by hand, which requires much time and complicated work.

SUMMARY OF THE INVENTION

It is an object of the present invention to overcome the shortcomings discussed above.

It is another object of the present invention to provide methods and apparatus for locating coating faults on buried metal pipes with a higher precision and more convenient operation than in previous techniques.

In order to achieve the above and other objects, a coating fault locating technique according to the invention transmits a base electric signal from a power source to the buried metal pipe. A location of a coating fault in the buried pipe is detected by detecting a gradient of a changing magnetic field between two points spaced along the buried pipe. The gradient is detected based upon the output differential of at least one pair of search coils. The gradient is caused by a leakage of current that occurs at the coating fault.

In particular, the at least one pair of search coils are provided in a mobile unit that is located above ground. The at least one pair of search coils are spaced apart from one another and have their axes arranged so as to have a low sensitivity to a magnetic field generated by the base electric signal running through the buried pipe. The at least one pair of coils are spaced apart from each other such that a line drawn between midpoints of the search coils' axes crosses a plane normal to the axis of the buried pipe.

For example, the at least one pair of search coils are spaced from each other horizontally, with each coil arranged with its axis extending in a vertical plane.

According to a preferred embodiment, data detected by the search coils in the mobile unit is transmitted to a GPS system, which then generates a map identifying the locations of any detected coating faults.

An apparatus according to the invention includes structure to perform the method detailed above. According to one embodiment, the apparatus includes a base electric signal generator that generates a base electric signal in a buried pipe. The apparatus also includes a movable carriage on which at least one pair of search coils are mounted. The movable carriage is movable in a direction along the buried pipe. The at least one pair of search coils are spaced from each other to detect a gradient of a magnetic field along a length of the buried pipe.

A detector unit synchronously detects an output differential of the at least one pair of search coils based upon a reference signal. The reference signal can be the base electric signal, which is transmitted to the buried pipe and to the detector unit. Alternatively, the detector unit can receive the reference signal by detecting the base electric signal in the buried pipe. For example, the movable carriage can include monitor coils that electromagnetically detect the base electric signal in the buried pipe. As another alternative, the base electric signal can be provided to the detector unit from the base electric signal generator via either a hardwired coupling or via radiowaves.

The detector unit can transmit data relating to detected coating faults to a Global Positioning System (GPS), which then transmits data to a monitor or printing device, to generate a map indicating locations of the coating faults.

BRIEF DESCRIPTION OF THE DRAWINGS

The invention will be described in detail with reference to the following drawings in which like reference numerals refer to like elements and wherein:

FIG. 9 is a block, circuit diagram showing the analyzing and indicating/recording part of the invention including linkage to a GPS;

DETAILED DESCRIPTION OF PREFERRED EMBODIMENTS

According to the present invention, a base electric signal generator applies a base electric signal to buried metal pipe, such as, for example a buried steel gas pipeline. The base electric signal applied to the buried steel pipe results in a magnetic field being generated from the buried steel pipe. Any coating faults in the buried pipe, which can lead to (or be caused by) corrosion of the pipe, result in current (known as leakage current) leaking from the buried steel pipe. This leakage current creates a magnetic field part orthogonal to the magnetic field generated from the buried pipe.

According to the invention, at least one pair of search coils provided above ground, for example in a movable carriage, detect this orthogonal magnetic field part caused by the leakage current. In particular, the at least one pair of search coils are spaced apart from each other, for example, along the length of the buried pipe. The axes of the search coils are oriented so that they are sensitive to magnetic fields in the orthogonal direction (i.e., magnetic fields due to the leakage current) of the pipe. A detector unit receives outputs from the search coils and, using a reference signal, which is based on the base electric signal, detects the orthogonal magnetic field. In particular, the detector uses 90 degree orthogonal synchronous detection.

The reference signal can be directly supplied to the detector unit by the base electric signal generator. This can be a hard-wire transmission or a radiowave transmission. Alternatively, the reference signal can be supplied by detecting the base electric signal in the buried steel pipe. For example, the movable carriage can include appropriately arranged monitor coils that detect the base electric signal in the buried steel pipe. As another alternative, an additional electric signal generator that generates the reference signal having the same frequency as that of the base electric signal generated by the base electric signal generator can be provided, for example, at the search location. In this case, prior to detection, the additional generator and the base generator 7 are synchronized.

Furthermore, it is preferable to provide a Global Positioning System (GPS) that receives data relating to the location of detected coating faults. The GPS then generates a map (either on a monitor or on paper) that identifies the coating faults.

Figure 1:
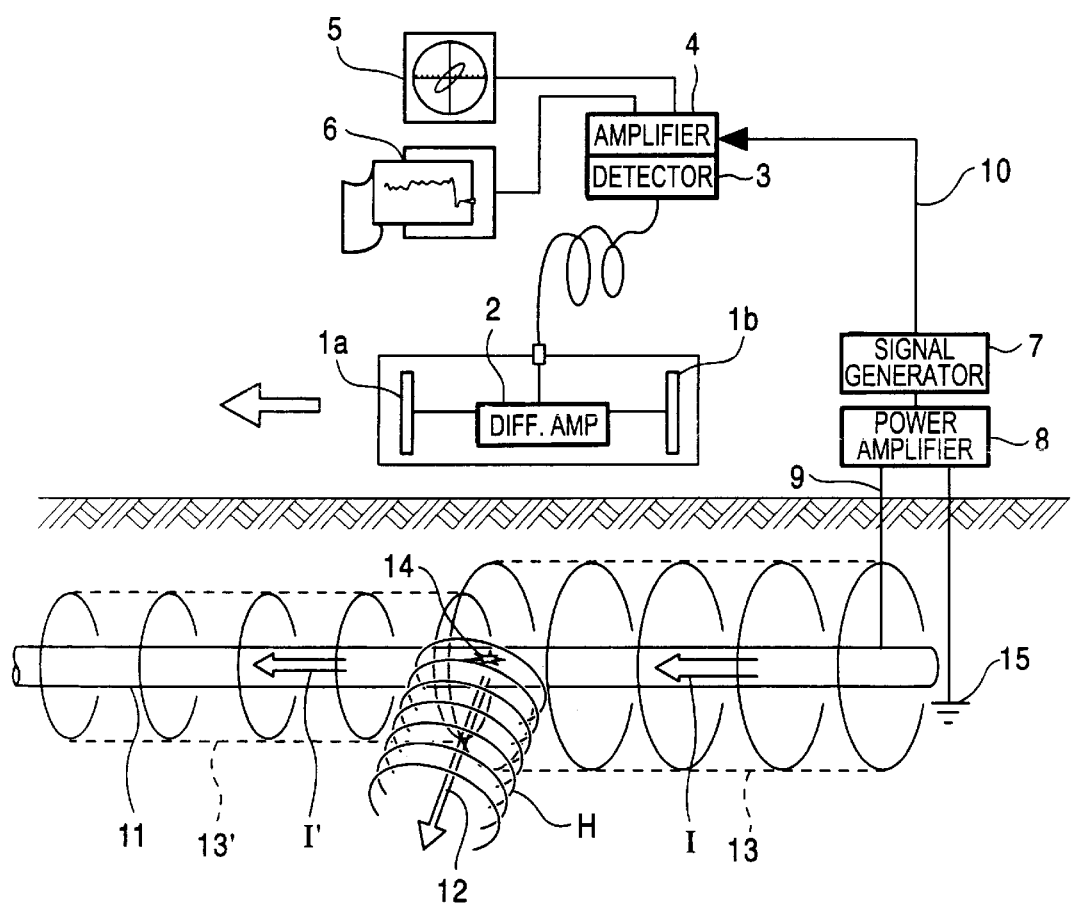
FIG. 1 is a schematic view of an apparatus for locating coating faults on buried steel pipelines according to one embodiment of the invention.

FIG. 1 is a schematic diagram of an apparatus for locating coating faults on buried pipes according to an embodiment of the invention. A base electric signal generator 7 sends the base electric signal to buried steel pipe 11 via a power amplifier 8. In particular, a base electric signal line 9 is attached between amplifier 8 and the buried steel pipe 11. The amplifier 8 also is attached to ground 15. The base electric signal causes a current I to run through the buried pipe 11, producing magnetic field 13.

A leakage current 12 is present due to a coating fault 14 in the buried pipe 11. The leakage current 12 always includes orthogonal part to the current I running in the buried steel pipe. Accordingly, the magnetic field H produced by the leakage current 12 includes orthogonal part to the magnetic field 13 produced by current I running through the buried pipe.

Due to leakage current 12, the current I' and its accompanying magnetic field 13' downstream of the coating fault 14 is less than the current I and magnetic field 13 upstream of the coating fault 14. Roughly speaking, I=I'+12.

At least one pair of search coils 1a and 1b are provided on a movable carriage, which is located above ground. The search coils 1a and 1b are coupled to a differential amplifier 2. The differential amplifier 2 is coupled to an amplifier 3, which is coupled to a detector 4. The detector 4 receives a reference signal (REF) 10 from base electric signal generator 7. The output of detector 4 is provided to any of various means for indicating the detected output, for example, an oscilloscope 5, etc., and to a recording means such as, for example a pen-recorder 6.

The magnetic field H caused by the leakage current 12 is converted into an induced electromotive force by the pair of search coils 1a and 1b. The search coils 1a and 1b have respective axes, 1a and 1b (see FIG. 2). The axes of the search coils are arranged in a direction so as to have a low sensitivity to the magnetic field (13 or 13') generated by the base electric signal running through the buried pipe. The search coils, however, are arranged in a direction so that they have a high sensitivity to the magnetic field H generated by the leakage current 12.

In particular, the search coils have a highest response when their axes are parallel to the direction of the magnetic field. Accordingly, the axes of the search coils are preferably arranged so as to be parallel to the magnetic field H generated by the leakage current 12, and at least a line interconnecting the center of the axes of the search coils is not in a plane orthogonal to the axis of the buried pipe. Accordingly, the search coils are arranged so as to have a low sensitivity to the magnetic field 13 generated by the base electric signal running in the buried pipe.

The output of each coil 1a and 1b is provided to the differential amplifier 2, the output differential of which is amplified by the amplifier 3. This signal is supplied to detector 4, which outputs to the oscilloscope 5 and/or the pen-recorder 6. This type of sensor device, which outputs a differential of each coil's output is referred to as differential-type search coils.

The base electric signal transmitted from the generator 7 can be sent to the buried pipe through the power amplifier 8, which is connected to ground, by, for example, an Mg electrode plate. The base electric signal can be provided to the buried pipe through terminals which are usually provided at the joints of the buried pipe, for example at intervals of 100–200 meters. These terminals are accessible through, for example, a manhole.

The direction of the magnetic flux in the magnetic field H generated by the leakage current 12 is not constant because the direction of the current can change. Accordingly, it is preferable to provide more than one pair of search coils, with each pair extending in different directions. Thus, FIG. 1 shows the minimum, single pair of search coils. While the search coils 1a and 1b in FIG. 1 are oriented to extend vertically, the additional pairs, for example, can extend at an angle between horizontal and vertical. It is also preferable, for example, to use a pair of coils that extend vertically and a pair of coils that are parallel to the direction of the buried pipe.

Figure 2:
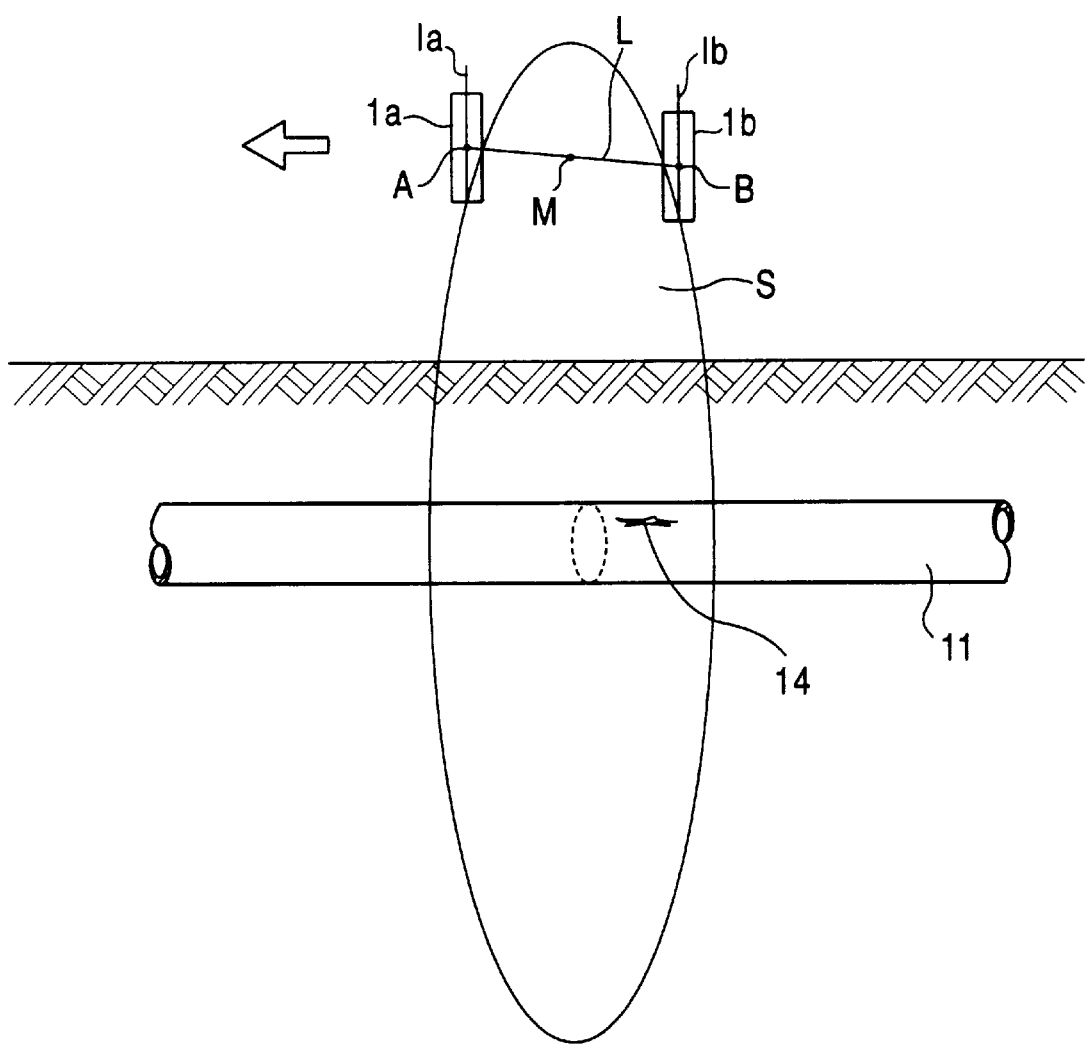
FIG. 2 is a schematic representation showing positional relationships between one pair of search coils and a buried pipe.

FIG. 2 illustrates the manner in which the coils are arranged relative to the buried pipe 11. The coils 1a and 1b are provided on a movable carriage (not shown in FIG. 2) that is movable in the direction of the arrow in FIG. 2. The search coils 1a and 1b are arranged so that their axes 1a and 1b are spaced from each other in the horizontal direction in FIG. 2. The search coils 1a and 1b are arranged so that when the carriage is moved, a straight line L drawn through the center points A and B in the longitudinal direction of the axes 1a and 1b of the two coils crosses a plane S normal to the axis of the buried pipe at point M.

The use of the alternating current facilitates the synchronous detection technique. Moving the two coils enables one to find the gradient of the change in the magnetic field between two points along the buried steel pipe.

In this case, if there are no coating faults, the magnetic field generated by the current caused by the base electrical signal is almost constant. Accordingly, there is virtually no differential of the induced electromotive force in the search coils. However, when there is a coating fault, a disorder of a magnetic field locally generated by the leakage current exists, and is detected because the differential of the electromotive force in the search coils changes. As the pair of search coils 1a and 1b are arranged in the same direction and are maintained at a constant interval, the detection of the gradient of the change in magnetic field between this interval can be found. With prior magnetic field-detecting methods, it was difficult to detect a small change in the magnetic field because only absolute values were considered.

However, the present invention theoretically increases the precision of the detection while removing same-phase noise by using the output differential and by orienting the coils so that they are highly sensitive only to the leakage current. The present arrangement also is advantageous because it is arranged to detect the small amount of leakage current and can distinguish a temporary change in the magnetic field (i.e., a disorder in the magnetic field) created by the coating fault.

The present invention also is advantageous because it uses, as REF signal 10, a signal that is related to the base electric signal provided to the buried pipe 11. In prior systems using a reference signal that is not related to the base electric signal applied to the buried pipe, there were many difficulties and mistakes made due to the difficulty in distinguishing the magnetic field created by the base electric signal and magnetic fields created from external sources, for example, environmental noise in the 50\60 Hz range.

The present invention relies upon synchronous detection in which the base electric signal that is applied to the buried pipe also is applied to the differential amplifier 2 output. Using this technique, a phase deviation of the differential output relative to the base electric signal can be found and distinguished from environmental noises. That is, any phase differential of the electromotive force in the search coils changes in synchronism with any changes of the magnetic field generated by the base electric signal running through the buried pipe.

It is preferable to use a base electric signal having a frequency that is not an integer multiple of a common commercial frequency such as, 50\60 Hz.

With respect to the coating fault location operation, from the viewpoint of working efficiency, it would be better to provide the amplifier 3, the detector 4, the means for detecting the output 5, and the means for recording the output 6, along with the search coils 1a and 1b and the differential amplifier 2 in a mobile unit. With such an arrangement, the REF signal 10 must be transmitted from the generator 7 to the mobile unit. This can be done via radiowaves, for example.

A preferred radiowave transmission frequency for the base electric signal is less than or equal to 100 KHz, even more preferably between about 220 Hz and 820 Hz, in order to reduce noise.

Figure 3:
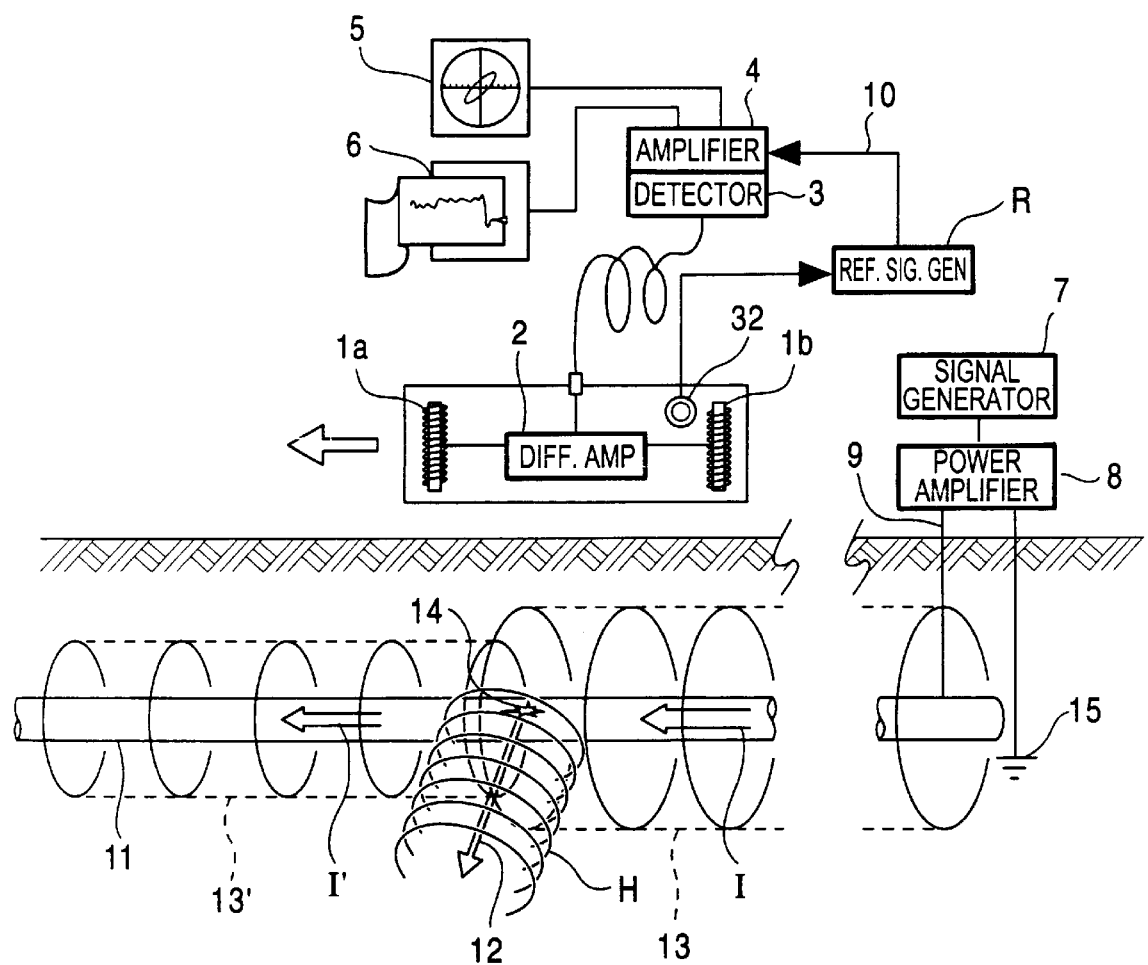
FIG. 3 is a schematic view of an apparatus for locating coating faults in buried steel pipes according to a second embodiment of the invention.

FIG. 3 illustrates an embodiment in which the REF signal 10 is generated by a reference signal generator R provided at the search location (i.e., on the mobile unit). In this embodiment, reference signal generator R detects the base signal from the buried pipe 11 using monitor coils 32 provided on the mobile unit. However, the manner in which the REF signal 10 is generated is not limited to the above two examples.

The present invention is also advantageous, as will be described below, when it is used in combination with a GPS to output a map that identifies detected coating faults.

EXAMPLES

Figure 4:
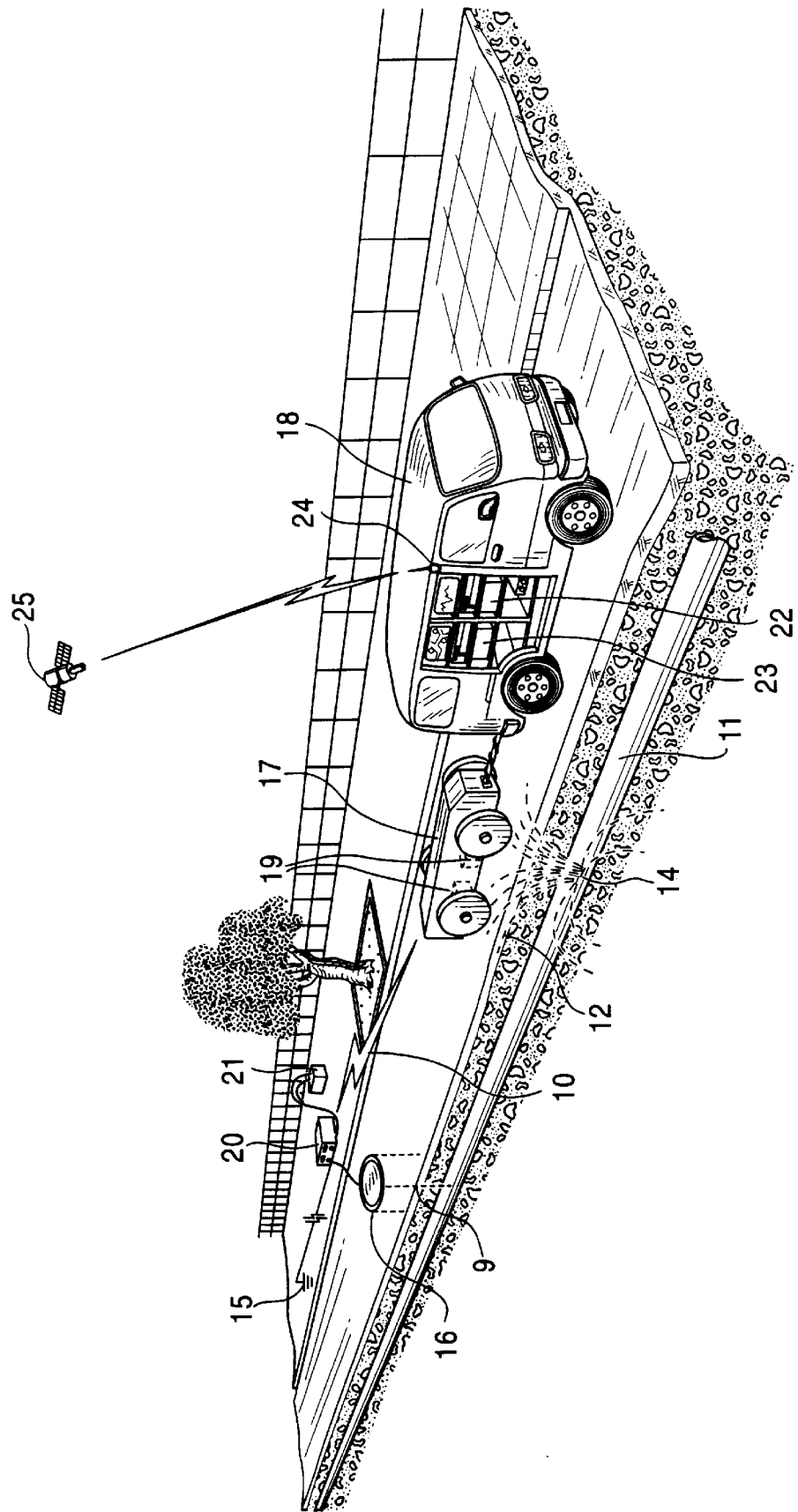
FIG. 4 is a perspective view of an apparatus for locating coating faults in buried steel pipes according to the invention.

FIG. 4 illustrates one arrangement of an apparatus for locating coating faults in buried steel pipes according to an embodiment of the invention. A transmitter 20 includes base electric signal generator 7 and power amplifier 8. A power supply 21 provides power to transmitter 20. The base electric signal is output from transmitter 20 via a cable, for example, which is passed through a manhole 16 and attached to the buried pipe 11. A mobile unit 17 includes the receiving and detecting unit 19. A vehicle 18 such as a van includes an analyzing and indicating/recording unit 22 and a GPS unit 23. GPS unit 23 includes a GPS antenna 24 which communicates with a satellite 25. The other elements are the same as similarly referenced elements in FIG. 1.

As shown in FIG. 4, the transmitter 20 and power supply 21 are located near a manhole 16. The receiving and detecting unit 19 is provided in the mobile unit 17 which is pulled by vehicle 18. The REF signal 10 is transmitted to the mobile unit 17 via radiowaves.

Recently, GPS are well known and used as car navigation systems. GPS are capable of generating map data and are capable of indicating the present location of the GPS antenna 24. Accordingly, when coating faults are detected, this data is supplied to the GPS so that the map can mark (either on a monitor or on a printout) the location of the coating fault. Placement of GPS antenna 24 on the mobile unit 17 would further increase the accuracy of the resulting map.

Figure 5:
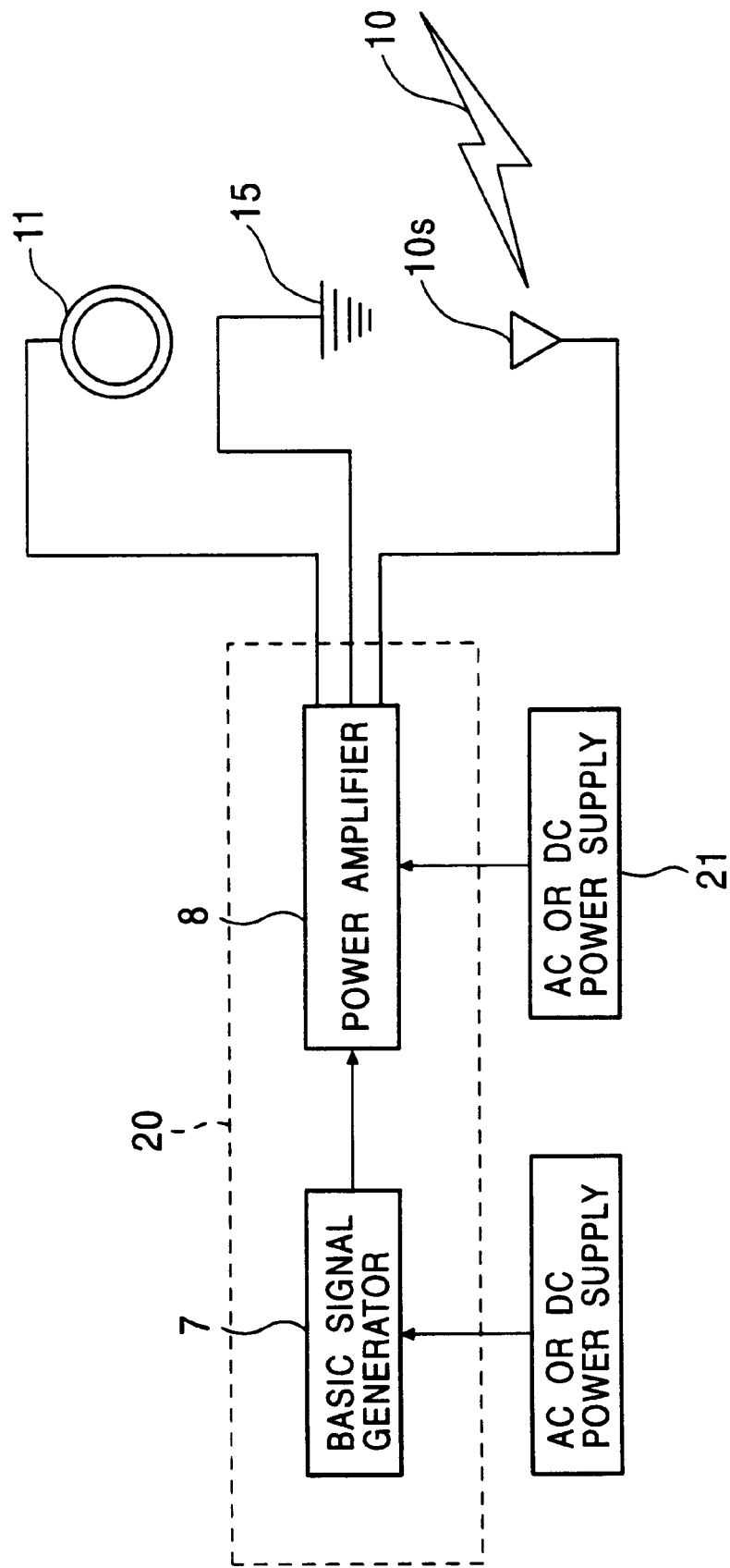
FIG. 5 is a block, circuit diagram showing the system for generating and transmitting a base electric signal.

FIG. 5 is a block circuit diagram of the base electric signal transmitter 20. The elements are the same as those described in FIGS. 1–4. A REF signal transmitter 10s transmits the base electric signal via radiowaves to, for example, the mobile unit 17. In this example, a transmitting frequency of 725 Hz is used for the REF signal 10.

Figure 6:
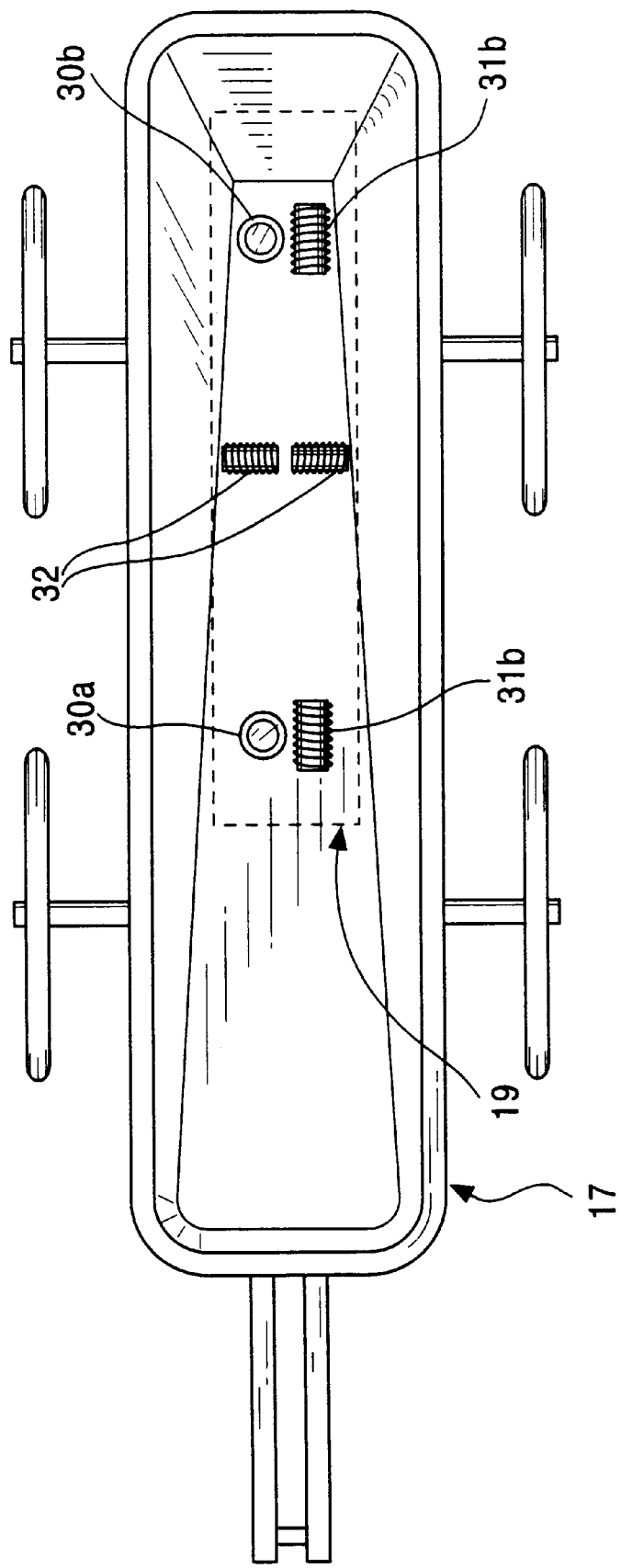
FIG. 6 is a plan view of a movable carriage, and illustrates pairs of search coils and a pair of monitor coils.

FIG. 6 is a plan view showing the position of the search coils on the mobile unit 17. In this embodiment, two pairs of search coils are provided. Vertical search coils 30a and 30b are vertical relative to the road surface. Horizontal search coils 31a and 31b are parallel to the road surface, with their axes extending parallel to the moving direction of the mobile unit 17. The coils of each pair are separated from each other by 1 meter in the moving direction of the mobile unit 17. Monitor coils 32, which detect the base electric signal in the buried pipe, are arranged so as to be orthogonal to the search coils and located centrally between the search coils 30a, 31a and 30b, 31b.

Figure 7:
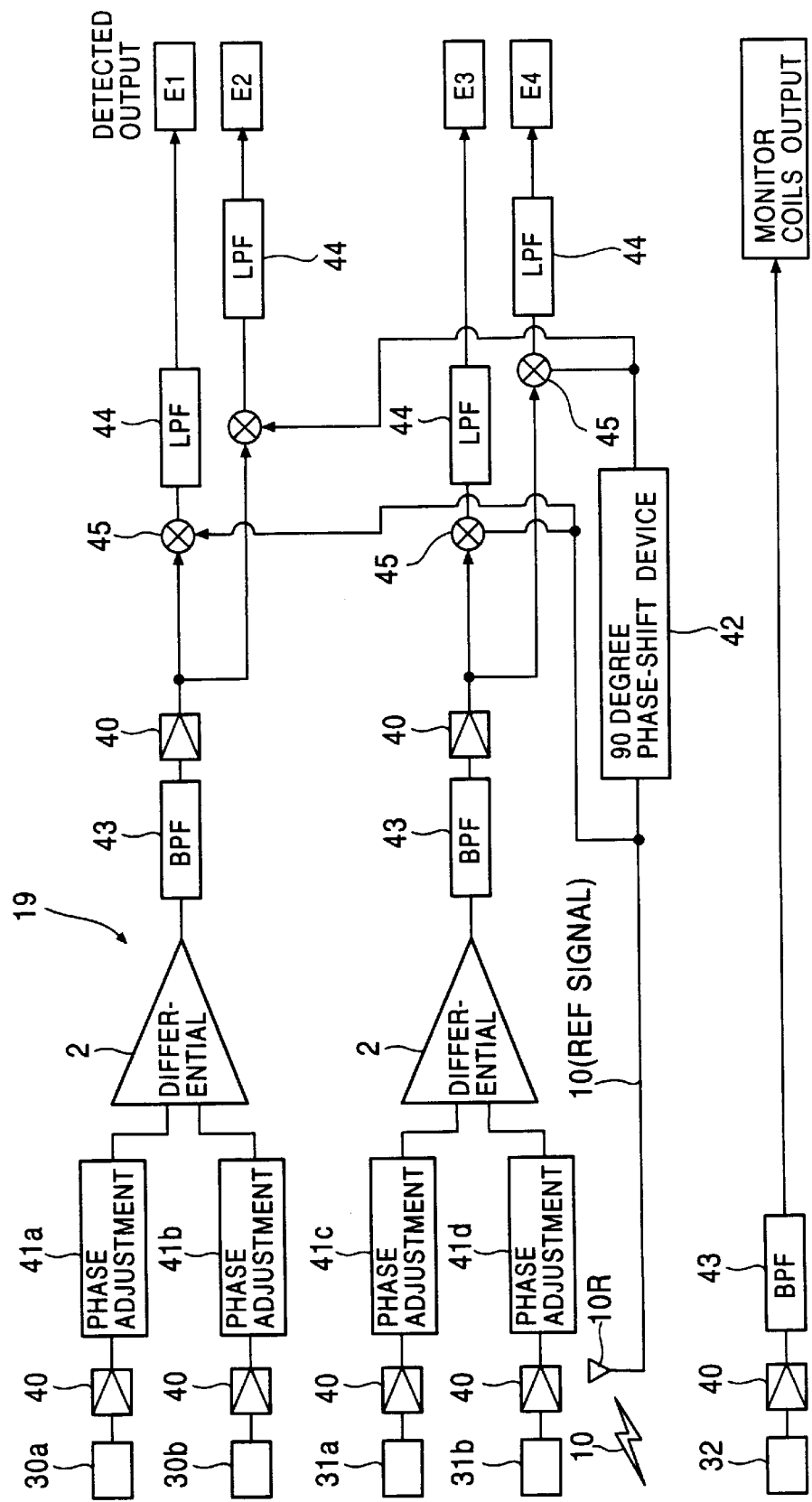
FIG. 7 is a block, circuit diagram of a receiving and detecting portion of an embodiment of the invention.

FIG. 7 is a block, circuit diagram showing the receiving and detecting unit 19. REF signal receiver 10R receives the REF signal 10 transmitted via radiowaves. The receiving and detecting unit 19 also includes amplifiers 40, phase adjustment devices 41a, 41b, 41c and 41d, 90 degree phase-shift device 42, band-pass-filters (BPF) 43, low-pass-filters (LPF) 44, and multiplication circuits 45 in the arrangement illustrated in FIG. 7. Reference numerals E1–E4 illustrate the detected outputs.

The output of vertical coils 30a, 30b and or horizontal coils 31a and 31b is sent to the differential amplifier 2 via the phase adjustment devices 41a–d so as to lose any differences in phases after passing through amplifier 40. The differential amplifier 2 outputs the difference between the phase adjustment devices 41a and 41b and the phase adjustment devices 41c and 41d. These output differentials are output to the BPF 43, the amplifier 40, and finally synchronously detected by using the 90 degree phase-shift device 42.

This 90 degree orthogonal synchronous detection technique separates the output differential of each coil pair 30, 31. These values then are multiplied by the REF signal in the multiplication circuit 45 to provide the detected outputs E1 and E3 through the LPF 44. The other multiplication circuit 45 multiplies by the REF signal 10 after it is shifted by 90 degrees by passing the REF signal 10 through the 90 degrees phase-shift device 42, to produce the detected outputs E2 and E4 through the LPF 44.

Figure 8:
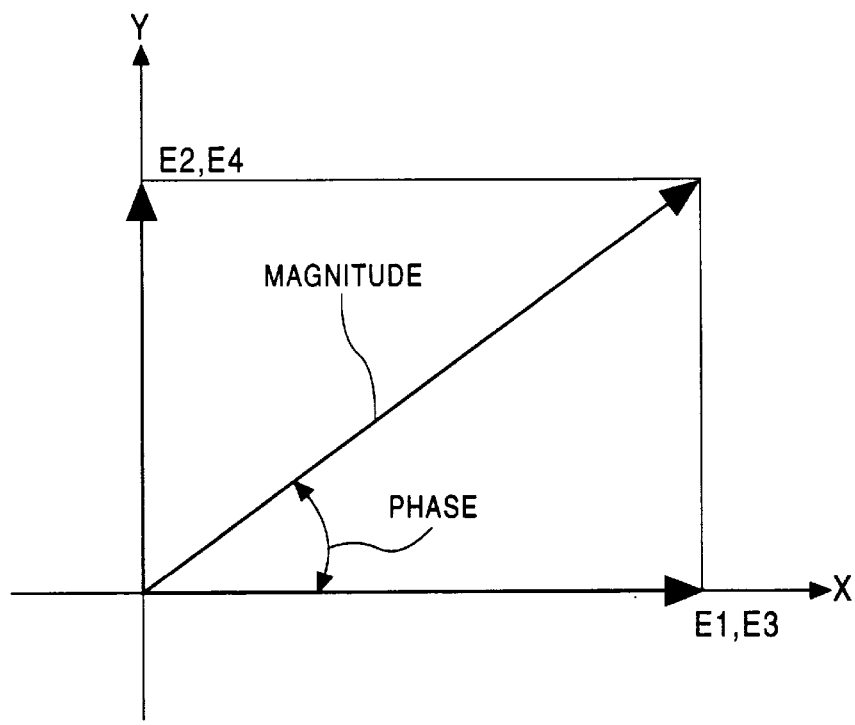
FIG. 8 is a graph that explains the magnitude and phase of an output differential of the search coils.

As shown in FIG. 8, the outputs E1 and E2 of the vertical search coils (30a and 30b) are plotted along the x axis and y axis, respectively, while the outputs E3 and E4 of the horizontal coils (31a and 31b) are plotted along the x axis and the y axis, respectively. This enables the magnitude and phase of each paired coil output differential to be displayed.

In many tests conducted by the inventors, it is clear that the detected output coating fault has a phase-shift. As the present invention can simultaneously estimate the magnitude and phase of each coil pair output differential, the location of coating faults can be found with a higher precision than in previous devices that only roughly detected the magnitude of the magnetic field.

As further shown in FIG. 7, when monitor coils 32 are included, the monitor coil output is amplified by amplifier 40, sent through the BPF 43 and output as the monitor coil output.

FIG. 9 is a block circuit diagram showing the analyzing and indicating\recording unit and the GPS unit. The analyzing unit includes an A\D and D\A (analog-to-digital and digital-to-analog converter), a CPU (central processing unit) and a VDT (Video Display Terminal). An interface couples the analyzing part with the indicating\recording part and the GPS.

The detected outputs E1–E4 from the receiving and detecting unit 19 and the monitor coil output 32 is provided to the A\D and D\A converter as analog signals. These are converted to digital signals. The CPU processes the data and provides it to the indicating means (e.g., the oscilloscope) and\or to the recording means (e.g., the pen-recorder). The CPU also can combine the data representing locations of coating faults with map data provided by the GPS via the VDT so as to indicate the location of coating faults on a map.

Figure 10:
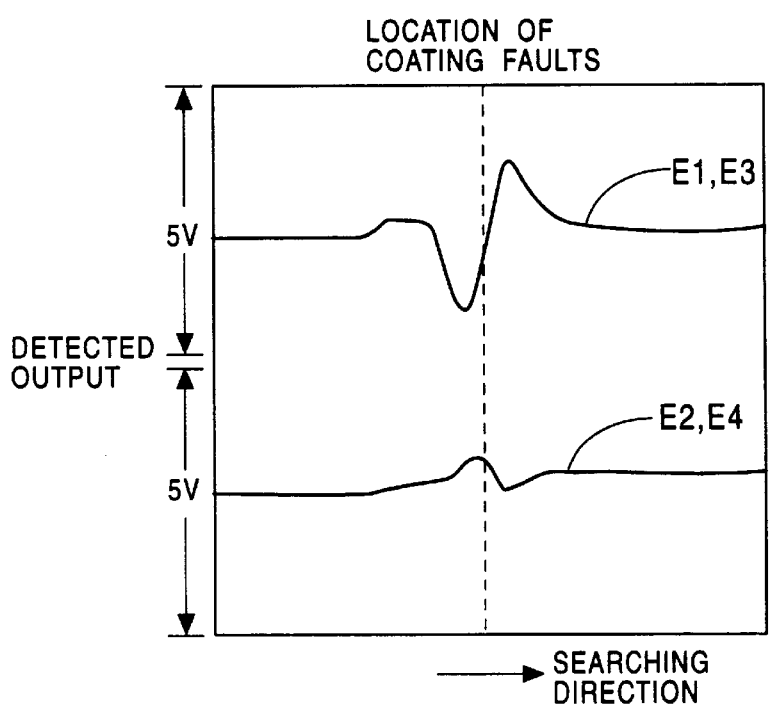
FIG. 10 shows the detected output of a coating fault recorded on a chart by a pen-recorder.

FIG. 10 illustrates the output of a pen-recorder based upon data E1–E4. As can be seen by FIG. 10, the location of coating faults are easily detected based upon a disruption in the output.

Figure 11:
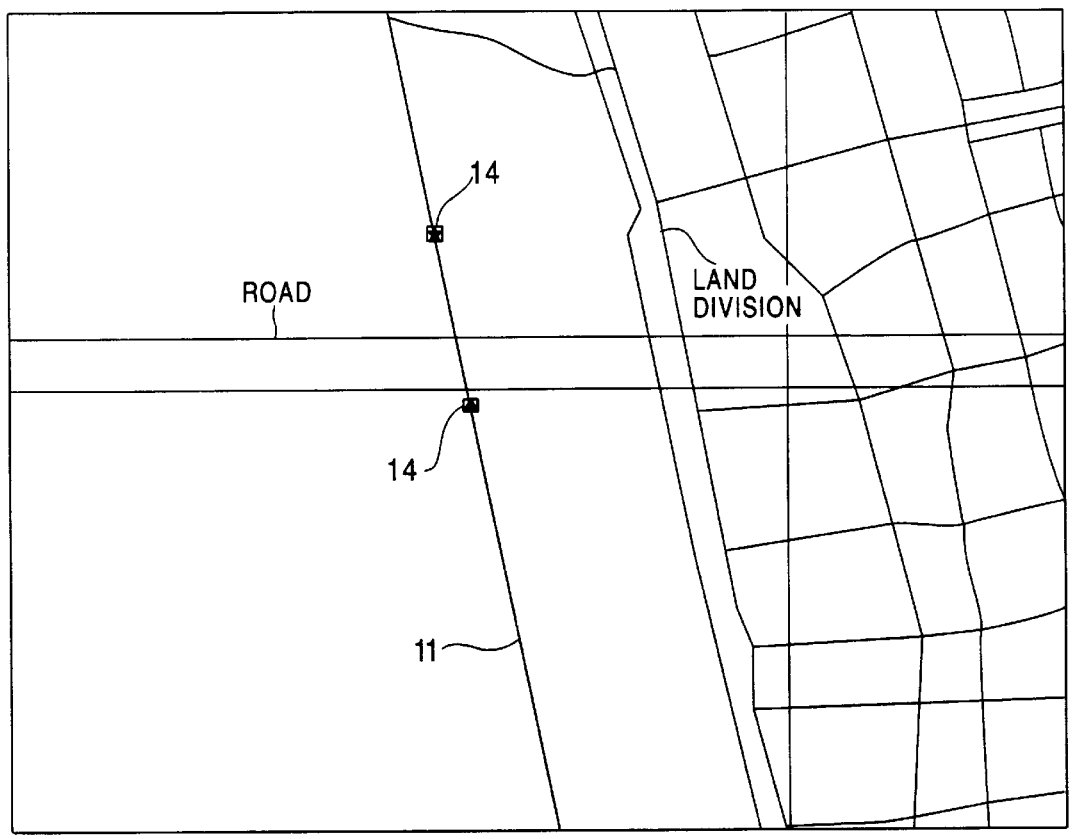
FIG. 11 illustrates a map that identifies the location of coating faults generated by a GPS.

FIG. 11 illustrates a map generated by the GPS and identifying coating faults thereon. There are two coating faults identified on this map. This enables the searching operation to become more efficient because the data relating to locations of coating faults are quickly processed and output on a map.

The present invention provides a higher precision apparatus and method for locating coating faults on buried pipelines than possible with previous methods. This is achieved by detecting local disorders of a magnetic field generated by leakage current from coating faults. As described above, the local disorder is detected by at least one pair of search coils. Additionally, a 90-degree orthogonal synchronization technique is used to detect an output differential of the search coils while using a base electric signal that is transmitted to the buried pipe as a reference signal. The system simultaneously estimates the magnitude and phase of each pair of coil output differential and is able to detect only the magnetic field generated from the leakage current, without being interfered with by environmental noise.

Additionally, by transmitting data via radiowaves to a GPS, map data is readily generated that identifies locations of the coating faults.

While this invention has been described in conjunction with specific embodiments thereof, it is evident that many alternatives, modifications and variations will be apparent to those skilled in the art. Accordingly, the preferred embodiments of the invention set forth herein are intended to be illustrative, not limiting. Various changes may be made without departing from the spirit and scope of the invention as defined in the following claims.

What is claimed is:

1. A method of locating coating faults on a buried pipe, comprising the steps of:

transmitting a base electric signal from a source to the buried pipe; and detecting a location of coating faults on the buried pipe by detecting a gradient of a changing magnetic field between two points along the buried pipe caused by a leakage of current from the coating faults based upon an output differential of at least one pair of search coils, each coil of the at least one pair of search coils arranged so that axes of the search coils are spaced from each other by a distance in a direction along a length of the buried pipe such that a line interconnecting the axes of the search coils crosses a plane orthogonal to an axis of the buried pipe.

2. The method of claim 1, wherein the detecting step includes:

arranging the axes of the search coils so as to have a low sensitivity to a magnetic field generated by the base electric signal running in the buried pipe;

moving the at least one pair of search coils along a direction of the buried pipe; and finding a disorder of a magnetic field generated by the leakage current from the coating fault in the buried pipe by finding an output differential of the at least one pair of search coils, wherein the base electric signal is used as a reference signal to synchronously detect the output differential of the at least one pair of search coils.

3. The method of claim 2, wherein the reference signal is transmitted from the source via radiowaves to a unit that synchronously detects the output differential of the search coils.

4. The method of claim 2, wherein the reference signal is generated at a location of the search coils by detecting the base electric signal running in the buried pipe using monitor coils.

5. The method of claim 2, wherein the reference signal is generated by an additional electric signal generator that generates the reference signal to have a same frequency as the base electric signal.

6. The method of claim 2, wherein the synchronous detecting uses a 90 degree phase difference between outputs of the search coils.

7. The method of claim 1, further comprising the step of identifying locations of the coating faults on a map using a Global Positioning System.

8. An apparatus for locating coating faults on a buried pipe, comprising:
- a movable carriage, at least one pair of search coils mounted on the movable carriage, the at least one pair of search coils spaced from each other in a moving direction of the movable carriage; and
- a base electric signal generator that applies a base electric signal to a buried pipe, wherein the at least one pair of search coils detects a gradient of a magnetic field resulting from leakage of current through coating faults in the buried pipe.

9. The apparatus of claim 8, further comprising a pair of monitor coils mounted on the movable carriage to detect the base electric signal in the buried pipe.

10. The apparatus of claim 8, wherein axes of the at least one pair of coils are oriented so as to have a low sensitivity to a magnetic field generated by the base electric signal running in the buried pipe.

11. The apparatus of claim 8, further comprising:
- a detector coupled to the at least one pair of search coils, the detector executing synchronous detection of an output differential of the at least one pair of search coils by using a reference signal that is based on the base electric signal.

12. The apparatus of claim 11, wherein the base electric signal generator includes a radiowave emitter, the detector includes a radiowave receiver, and the base electric signal is transmitted from the base electric signal generator to the detector by radiowaves.

13. The apparatus of claim 11, wherein the detector includes a pair of monitor coils that detect the base electric signal running in the buried pipe, the reference signal being based upon the detected base electric signal.

14. The apparatus of claim 11, wherein the detector includes an additional electric signal generator that generates the reference signal so as to have a same frequency as the base electric signal.

15. The apparatus of claim 8, further comprising means for visually indicating outputs of the at least one pair of search coils.

16. The apparatus of claim 15, wherein the means for visually indicating includes an oscilloscope.

17. The apparatus of claim 15, wherein the means for visually indicating includes a pen recorder.

18. The apparatus of claim 15, wherein the means for visually indicating generates a map on which the detected coating faults are identified.

19. The apparatus of claim 8, further comprising a Global Positioning System coupled to the at least one pair of search coils to generate a map on which the coating faults are identified.

20. A method of locating coating faults on a buried pipe, comprising the steps of:
- supplying a base electric signal from a source to the buried pipe;
- moving a movable carriage above ground in a vicinity of the buried pipe, the movable carriage including at least one pair of search coils that are spaced from each other in a movement direction of the movable carriage; and
- detecting a location of coating faults on the buried pipe based on currents induced in the at least one pair of search coils by a changing magnetic field caused by a leakage of current, caused by the supplied base electric signal, from the coating faults.

21. The method of claim 20, wherein:
- each search coil of the at least one pair of search coils is arranged on the movable carriage so that axes of the search coils are spaced from each other by a distance in a direction such that a line interconnecting the axes of the search coils crosses a plane orthogonal to an axis of the buried pipe, the axes being arranged so as to have a low sensitivity to a magnetic field generated by the base electric signal running in the buried pipe;
- the moving step includes moving the at least one pair of search coils along a direction of the buried pipe; and
- the detecting step includes finding a disorder of a magnetic field generated by the leakage current from the coating fault in the buried pipe by finding an output differential of the at least one pair of search coils, wherein the base electric signal is used as a reference signal to synchronously detect the output differential of the at least one pair of search coils.

22. The method of claim 20, further comprising the step of identifying locations of the coating faults on a map using a Global Positioning System.

23. A method of locating coating faults on a buried pipe, comprising the steps of:
- detecting at least one coating fault on a buried pipe by moving a movable carriage containing a coating fault detector above ground in the vicinity of the buried pipe;
- transmitting position data of a position where the at least one coating fault was located to a Global Positioning System; and
- generating a map that indicates the position of the at least one coating fault using data from the Global Positioning System.

24. An apparatus for locating coating faults on a buried pipe, comprising:
- a movable carriage containing a coating fault detector, the movable carriage being movable above ground in the vicinity of the buried pipe to detect coating faults in buried pipe;
- means for transmitting position data of a position where the at least one coating fault was located to a Global Positioning System; and
- means for generating a map that indicates the position of the at least one coating fault using data from the Global Positioning System.

* * * * *